US011413285B2

(12) United States Patent
Daemmgen et al.

(10) Patent No.: US 11,413,285 B2
(45) Date of Patent: *Aug. 16, 2022

(54) PDE III INHIBITORS FOR TREATMENT OF ASYMPTOMATIC HEART FAILURE

(71) Applicant: Boehringer Ingelheim Vetmedica GmbH, Ingelheim am Rhein (DE)

(72) Inventors: Juergen Daemmgen, Ochsenhausen (DE); Olaf Joens, Ober-Hilbersheim (DE); Rainer Kleemann, Ingelheim am Rhein (DE); Christian Troetschel, Waldalgesheim (DE); Andrea Vollmar, Wissen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/127,921

(22) Filed: Sep. 11, 2018

(65) Prior Publication Data

US 2019/0008862 A1 Jan. 10, 2019

Related U.S. Application Data

(63) Continuation of application No. 13/832,292, filed on Mar. 15, 2013, now Pat. No. 10,117,869, which is a continuation of application No. 12/482,481, filed on Jun. 11, 2009, now Pat. No. 8,980,894, which is a continuation-in-part of application No. 11/559,467, filed on Nov. 14, 2006, now abandoned, and a continuation-in-part of application No. 11/087,465, filed on Mar. 23, 2005, now Pat. No. 9,463,199.

(30) Foreign Application Priority Data

Mar. 25, 2004 (EP) ..................... 04007179
Nov. 14, 2005 (EP) ..................... 05110689

(51) Int. Cl.
| | |
|---|---|
| *A61K 31/501* | (2006.01) |
| *A61P 9/04* | (2006.01) |
| *A61K 31/4166* | (2006.01) |
| *A61K 31/4412* | (2006.01) |
| *A61K 31/4427* | (2006.01) |
| *A61K 31/444* | (2006.01) |
| *A61K 31/341* | (2006.01) |
| *A61K 31/40* | (2006.01) |
| *A61K 31/55* | (2006.01) |
| *A61K 31/7048* | (2006.01) |

(52) U.S. Cl.
CPC .......... *A61K 31/501* (2013.01); *A61K 31/341* (2013.01); *A61K 31/40* (2013.01); *A61K 31/4166* (2013.01); *A61K 31/444* (2013.01); *A61K 31/4412* (2013.01); *A61K 31/4427* (2013.01); *A61K 31/55* (2013.01); *A61K 31/7048* (2013.01); *A61P 9/04* (2018.01)

(58) Field of Classification Search
CPC .......... A61K 31/501; A61K 31/50; A61P 9/04
See application file for complete search history.

(56) References Cited

U.S. PATENT DOCUMENTS

| | | | |
|---|---|---|---|
| 3,574,859 | A | 4/1971 | Kosti |
| 3,822,349 | A | 7/1974 | Kosti |
| 3,832,460 | A | 8/1974 | Kosti |
| 3,839,522 | A | 10/1974 | Kosti |
| 3,950,333 | A | 4/1976 | Durant et al. |
| 4,128,658 | A | 12/1978 | Price et al. |
| 4,256,743 | A | 3/1981 | Goldhaber |
| 4,283,400 | A | 8/1981 | von Bittera et al. |
| 4,283,408 | A | 8/1981 | Hirata et al. |
| 4,293,557 | A | 10/1981 | Shibata et al. |
| 4,361,563 | A | 11/1982 | Austel et al. |
| 4,375,547 | A | 3/1983 | Pioch |
| 4,386,099 | A | 5/1983 | Cereda et al. |
| 4,427,648 | A | 1/1984 | Brickl et al. |
| 4,569,837 | A | 2/1986 | Suzuki et al. |
| 4,585,790 | A | 4/1986 | Padfield et al. |
| 4,596,705 | A | 6/1986 | Schepky et al. |
| 4,654,342 | A | 3/1987 | Slater |
| 4,704,284 | A | 11/1987 | Beatty et al. |
| 4,732,915 | A | 3/1988 | Ayer et al. |
| 4,851,226 | A | 7/1989 | Julian et al. |
| 4,865,851 | A | 9/1989 | James et al. |
| 4,868,182 | A | 9/1989 | Dage |
| 4,906,628 | A | 3/1990 | Coates |
| 4,933,182 | A | 6/1990 | Higashi et al. |
| 4,954,501 | A | 9/1990 | Herter et al. |
| 4,973,469 | A | 11/1990 | Mulligan et al. |
| 5,024,998 | A | 6/1991 | Bodor |

(Continued)

FOREIGN PATENT DOCUMENTS

| | | |
|---|---|---|
| AU | 2012101682 A4 | 1/2013 |
| CA | 950833 A1 | 7/1974 |

(Continued)

OTHER PUBLICATIONS

Lombard, 2000. Proceedings of the 18th American College of Veterinary Medicine Forum, p. 107-109.*

(Continued)

*Primary Examiner* — Zachary C Howard

(74) *Attorney, Agent, or Firm* — Andrew Aldag; John Ezcurra

(57) ABSTRACT

A method for treating a patient suffering from ISACHC Classification Class I heart failure includes administering to the patient a therapeutically effective amount of pimobendan or a pharmaceutically acceptable salt thereof, where the administration results in a reduction in the size of the patient's heart.

18 Claims, 4 Drawing Sheets

(56) References Cited

U.S. PATENT DOCUMENTS

| | | |
|---|---|---|
| 5,151,420 A | 9/1992 | Backstrom et al. |
| 5,188,836 A | 2/1993 | Muhammad et al. |
| 5,364,646 A | 11/1994 | Gruber et al. |
| 5,569,657 A | 10/1996 | Nore et al. |
| 5,571,533 A | 11/1996 | Santus et al. |
| 6,407,079 B1 | 6/2002 | Muller et al. |
| 6,476,078 B1 | 11/2002 | Jerussi et al. |
| 6,669,955 B2 | 12/2003 | Chungi et al. |
| 6,713,487 B2 | 3/2004 | Yu et al. |
| 7,262,165 B2 | 8/2007 | Lindenblatt et al. |
| 8,409,612 B1 | 4/2013 | Criere et al. |
| 8,846,679 B2 | 9/2014 | Folger et al. |
| 8,980,894 B2 * | 3/2015 | Daemmgen ........ A61K 31/4166 514/247 |
| 10,117,869 B2 * | 11/2018 | Daemmgen ........ A61K 31/4166 |
| 2003/0059471 A1 | 3/2003 | Compton et al. |
| 2003/0162835 A1 | 8/2003 | Staniforth et al. |
| 2003/0165565 A1 | 9/2003 | Mehta |
| 2003/0190343 A1 | 10/2003 | Thombre et al. |
| 2003/0212114 A1 | 11/2003 | Sato |
| 2004/0037869 A1 | 2/2004 | Cleverly et al. |
| 2004/0152664 A1 | 8/2004 | Chang et al. |
| 2004/0157887 A1 | 8/2004 | Whittle et al. |
| 2005/0095293 A1 | 5/2005 | Brauns et al. |
| 2005/0203097 A1 | 9/2005 | Folger et al. |
| 2005/0239692 A1 | 10/2005 | Lindenblatt et al. |
| 2007/0112010 A1 | 5/2007 | Kleeman et al. |
| 2008/0207629 A1 | 8/2008 | Folger et al. |
| 2009/0082282 A1 | 3/2009 | Daemmgen et al. |
| 2010/0035889 A1 | 2/2010 | Daemmgen et al. |
| 2010/0166857 A1 | 7/2010 | Fan et al. |
| 2010/0183718 A1 | 7/2010 | Ovaert et al. |
| 2010/0273807 A1 | 10/2010 | Kleeman et al. |
| 2011/0028457 A1 | 2/2011 | Roewer et al. |
| 2011/0189283 A1 | 8/2011 | Derrieu et al. |
| 2011/0251208 A1 | 10/2011 | Daemmgen et al. |
| 2011/0318420 A1 | 12/2011 | Hu et al. |
| 2012/0148640 A1 | 6/2012 | Folger et al. |
| 2012/0308662 A1 | 12/2012 | Konishi et al. |
| 2013/0115301 A1 | 5/2013 | Bele et al. |
| 2013/0203690 A1 | 8/2013 | Daemmgen et al. |
| 2014/0155338 A1 | 6/2014 | Daemmgen et al. |
| 2014/0235648 A1 | 8/2014 | Folger et al. |
| 2014/0363510 A1 | 12/2014 | Folger et al. |
| 2015/0025082 A1 | 1/2015 | Wen et al. |
| 2015/0064249 A1 | 3/2015 | Folger et al. |
| 2015/0148335 A1 | 5/2015 | Bova et al. |
| 2015/0150820 A1 | 6/2015 | Laczay |
| 2016/0038420 A1 | 2/2016 | Brunel et al. |
| 2017/0165260 A1 | 6/2017 | Folger et al. |
| 2017/0290829 A1 | 10/2017 | Schummer et al. |
| 2017/0368062 A1 | 12/2017 | Folger et al. |

FOREIGN PATENT DOCUMENTS

| | | | |
|---|---|---|---|
| CA | 1222697 | A1 | 6/1987 |
| CA | 1238277 | A | 6/1988 |
| CA | 2034569 | A1 | 7/1991 |
| CA | 1336498 | C | 8/1995 |
| CN | 1662250 | A | 8/2005 |
| CN | 1702243 | A | 11/2005 |
| DE | 3728244 | A1 | 3/1989 |
| DE | 1001623 | A1 | 7/1991 |
| EP | 0241179 | A1 | 10/1987 |
| EP | 0256566 | A1 | 2/1988 |
| EP | 0268146 | A1 | 5/1988 |
| EP | 0306846 | A2 | 3/1989 |
| EP | 0330052 | A2 | 8/1989 |
| EP | 0335545 | A2 | 10/1989 |
| EP | 0349657 | A1 | 1/1990 |
| EP | 439030 | A2 | 7/1991 |
| EP | 1123703 | A1 | 8/2001 |
| EP | 1247456 | A2 | 10/2002 |
| EP | 1260215 | A1 | 11/2002 |
| EP | 1579862 | A1 | 9/2005 |
| EP | 1903039 | A1 | 3/2008 |
| EP | 1920785 | A1 | 5/2008 |
| EP | 2338493 | A1 | 6/2011 |
| EP | 3034071 | A1 | 6/2016 |
| FR | 2350105 | A1 | 12/1977 |
| GB | 1045031 | A | 10/1966 |
| GB | 2228004 | A | 8/1990 |
| JP | 61500788 | A | 4/1986 |
| JP | H029825 | A | 1/1990 |
| JP | H03157314 | A | 7/1991 |
| JP | H0489428 | A | 3/1992 |
| JP | H0570612 | A | 3/1993 |
| JP | H11228302 | A | 8/1999 |
| JP | 2005281283 | A | 10/2005 |
| JP | 2007191419 | A | 8/2007 |
| JP | 2008504308 | A | 2/2008 |
| JP | 2011157390 | A | 8/2011 |
| JP | 2012533595 | A | 12/2012 |
| JP | 2013006798 | A | 1/2013 |
| JP | 2013503113 | A | 1/2013 |
| WO | 1985002767 | A1 | 7/1985 |
| WO | 1989004178 | A1 | 5/1989 |
| WO | 1995031963 | A1 | 11/1995 |
| WO | 0012137 | A1 | 3/2000 |
| WO | 2000069414 | A2 | 11/2000 |
| WO | 2001035925 | A1 | 5/2001 |
| WO | 2001064190 | A1 | 9/2001 |
| WO | 2001097861 | A2 | 12/2001 |
| WO | 0245693 | A1 | 6/2002 |
| WO | 2002049646 | A1 | 6/2002 |
| WO | 2003012030 | A2 | 2/2003 |
| WO | 03072141 | A1 | 9/2003 |
| WO | 2003074032 | A1 | 9/2003 |
| WO | 2003075895 | A1 | 9/2003 |
| WO | 2003097067 | A1 | 11/2003 |
| WO | 2003099194 | A2 | 12/2003 |
| WO | 2004000317 | A1 | 12/2003 |
| WO | 2004000344 | A1 | 12/2003 |
| WO | 2004016252 | A1 | 2/2004 |
| WO | 2004033444 | A1 | 4/2004 |
| WO | 2004037201 | A2 | 5/2004 |
| WO | 2004050657 | A2 | 6/2004 |
| WO | 2004058726 | A2 | 7/2004 |
| WO | 2004060353 | A1 | 7/2004 |
| WO | 2004089418 | A1 | 10/2004 |
| WO | 2005035505 | A2 | 4/2005 |
| WO | 2005084647 | A1 | 9/2005 |
| WO | 2005092343 | A1 | 10/2005 |
| WO | 2005107756 | A1 | 11/2005 |
| WO | 2005117911 | A2 | 12/2005 |
| WO | 2006000229 | A2 | 1/2006 |
| WO | 2006022562 | A1 | 3/2006 |
| WO | 2006060122 | A2 | 6/2006 |
| WO | 2006060127 | A2 | 6/2006 |
| WO | 2007036671 | A2 | 4/2007 |
| WO | 2007038796 | A1 | 4/2007 |
| WO | 2007054514 | A2 | 5/2007 |
| WO | 2007112274 | A2 | 10/2007 |
| WO | 2007128749 | A1 | 11/2007 |
| WO | 2008055871 | A1 | 5/2008 |
| WO | 2009060226 | A1 | 5/2009 |
| WO | 2010010257 | A2 | 1/2010 |
| WO | 2010055119 | A2 | 5/2010 |
| WO | 2010060874 | A1 | 6/2010 |
| WO | 2011009818 | A1 | 1/2011 |
| WO | 2011042463 | A2 | 4/2011 |
| WO | 2011076738 | A1 | 6/2011 |
| WO | 2011131259 | A1 | 10/2011 |
| WO | 2013024023 | A1 | 2/2013 |
| WO | 2013135852 | A1 | 9/2013 |
| WO | 2013164473 | A1 | 11/2013 |
| WO | 2013170317 | A1 | 11/2013 |
| WO | 2014136035 | A1 | 9/2014 |
| WO | 2015082389 | A1 | 6/2015 |
| WO | 2017174571 | A1 | 10/2017 |

(56) References Cited

OTHER PUBLICATIONS

Lewis, Alan B., "Clinical Profile and Outcome of Restrictive Cardiomyopathy in Children". American Heart Journal, vol. 123, No. 6, 1992, pp. 1589-1593.
Lezcano et al., "Complexation of Several Benzimidazole-Type Fungicides with Alpha and Beta-Cyclodextrins". Journal of Agricultural and Food Chemistry, vol. 50, 2002, pp. 108-112.
Lindenberg et al., "Classification of orally administered drugs on the World Health Organization Model list of Essential Medicines according to the biopharmaceutics classification system." European Journal of Pharmaceutics and Biopharmaceutics, vol. 58, 2004, pp. 265-278.
Lip et al., "ABC of heart failure: Aetiology". British Medical Journal, vol. 320, Jan. 2000, pp. 104-107.
Liu et al., "Cardiovascular Pathology: The Role of Cardiovascular Pathology in Practice". Textbook of Canine and Feline Cardiology: Principles and Clinical Practice, Second Edition, Chapter 36, Saunders, 1999, pp. 817-844.
Liu et al., "Pharmacology Preparation Technology." Chemical Industry Press, 2006, pp. 113-114.
Loew, Earl R., "Gastric Secretion in Dogs Treated with Histamine Antagonist, Thymoxyethyldiethylamine". Experimental Biology and Medicine, vol. 48, No. 1, Oct. 1941, pp. 65-68.
Loftsson et al., "Pharmaceutical Applications of Cyclodextrins. 1. Drug Solubilization and Stabilization". Journal of Pharmaceutical Sciences, vol. 85, No. 10, Oct. 1996, pp. 1017-1025.
Lombard et al., "Clinical Efficacy of Pimobendan Versus Benazepril for the Treatment of Acquired Atrioventricular Valvular Disease in Dogs". Journal of the American Animal Hospital Association, vol. 42, No. 4, Jul./Aug. 2006, pp. 249-261.
Lombard, Christophe W.,"Therapy of Congestive Heart Failure in Dogs with Pimobendan". Proceedings of the 18th Annual Veterinary Medical Forum, American College of Veterinary International Medicine, Seattle, WA, 2000, pp. 107-109.
Lord et al., "Radiology: Role of Radiology in Diagnosis and Management of Thoracic Disease". Textbook of Canine and Feline Cardiology: Principles and Clinical Practice, Second Edition, Chapter 7, Saunders, 1999, pp. 111-117.
Luis-Fuentes, Virginia, "The effect of pimobendan in English Cocker Spaniels and Doberman dogs with heart failure and idiopathic dilated cardiomyopathy (DCM)". Ingelheimer Dialog, Boehringer Inglehim Vetmedica GmbH, Jun. 2000, Frankfort/Mainz, pp. 8-11.
Lyon et al., "Near-Infrared Spectral Imaging for Quality Assurance of Pharmaceutical Products: Analysis of Tablets to Assess Powder Blend Homogeneity". AAPS PharmSciTech, vol. 3, No. 3, Art. 17, Sep. 2002, pp. 1-15.
Malik et al., "Permethrin Spot-On Intoxication of Cats: Literature review and survey of veterinary practitioners in Australia". Journal of Feline Medicine and Surgery, vol. 12, 2010, pp. 5-14.
Mamoru et al., "Effects of Long-term, Very-low-dose Pimobendan for Patients with Diastolic Heart Failure". Journal of Cardial Failure, vol. 12, No. 8, Oct. 2006, p. S171.
Matsumori et al., "Pharmacology letters: Accelerated Communication: Pimobendan inhibits the activation of transcription factor NF-kB A mechanism which explains its inhibition of cytokine production and inducible nitric oxide synthase". Life Sciences, vol. 67, 2000, pp. 2513-2519.
McCrohon et al., "Differentiation of Heart Failure Related to Dilated Cardiomyopathy and Coronary Artery Disease Using Gadolinium-Enhanced Cardiovascular Magnetic Resonance". Circulation, vol. 108, Jul. 2003, pp54-59. Originally published online Jun. 23, 2003, http://circ.ahajournals.org, 7 pages.
Medline, homogeneous, Merriam-Webster, Last Accessed Feb. 10, 2011, 1 page, http://www.merriam-webster.com/medlineplus/homogeneous.
Menard et al., "Physico-Chemical Aspects of the Complexation of Some Drugs with Cyclodextrins". Drug Development and Industrial Pharmacy, vol. 16, No. 1, 1990, pp. 91-113.
Merriam-Webster, homogeneous, Last Accessed Feb. 10, 2011, 2 pages, http://www.merriam-webster.com/dictionary/homogeneous.
Monnet et al., "Idiopathic Dilated Cardiomyopathy in Dogs: Survival and Prognostic Indicators". 1995, Journal of Veterinary Internal Medicine, vol. 9, No. 1, pp. 12-17.
Nainar et al., "Biopharmaceutical Classification System in In-vitro/In-vivo Correlation: Concept and Development Strategies in Drug Delivery." Tropical Journal of Pharmaceutical Research, vol. 11, No. 2, Apr. 2012, pp. 319-329.
Nakamoto et al., "The role of ascorbic acid deficiency in human gingivitis-a new hypothesis". Journal of Theoretical Biology, vol. 108, No. 2, May 1984, pp. 163-171.
Ng, Tien M.H., "Levosimendan, a New Calcium-Sensitizing Inotrope for Heart Failure". Pharmacotherapy, vol. 24, No. 10, 2004, pp. 1366-1384.
O'Grady, et al., "Does Angiotensin Converting Enzyme Inhibitor Therapy Delay the Onset of Congestive Heart Failure or Sudden Death in Doberman Pinschers with Occult Dilated Cardiomyopathy?" Acvim Abstracts, 1997, p. 138.
Ohte et al., "The Cardia Effects of Pimobendan (But Not Amrinone) Are Preserved at Rest and During Exercise in Conscious Dogs with Pacing-Induced Heart Failure". The Journal of Pharmacology and Experimental Therapeutics, vol. 282, No. 1, 1997, pp. 23-31.
Okazaki et al., "A genetic linkage map of the Syrian hamster and localization of cariomyopathy locus on chromosome 9qa2.1-b1 using RLGS spot-mapping" Nature Genetics, vol. 13, May 1996, pp. 87-90.
Ouellet et al., "Effect of Pimobendan on Echocardiographic Values in Dogs with Asymptomatic Mitral Valve Disease" Journal of Veterinary Internal Medicine, vol. 23, 2009, pp. 258-263.
Packer et al., "Effect Of Oral Milrinone On Mortality In Severe Chronic Heart Failure." The New England Journal of Medicine, vol. 325, No. 21, Nov. 1991, pp. 1468-1475.
Pagel et al., "Comparison of the effects of levosimendn, pimobendan, and milrinone on canine left ventricular-arterial coupling and mechanical efficiency". Basic Respiratory Cardiology, vol. 91, 1996, pp. 296-307.
Pagel et al., "Influence of levosimendan, pimobendan, and milrinone on the regional distribution of cardiac output in anaesthetized dogs". British Journal of Pharmacology, vol. 119,1996, pp. 609-615.
Permanetter et al., "Acute Effects of Intraveneous UD-CG 115 BS (Pimobendan) on the Cardiovascular System and Left Ventricular Pump Function". Journal of Cardiovascular Pharmacology, vol. 14, Supp. 2, 1989, pp. S36-S40.
Pernsteiner et al., "Effect of Topical Application of Phenylephrine Hydrochloride on Hyperplastic Gingivitis". Journal of Periodontology, vol. 48, No. 8, Aug. 1977, pp. 473-477.
Petit et al., "VETMEDIN® 1.25 mg, VETMEDIN® 5 mg, Chewable tablets, Inodilator (pimobendan) tablet for dogs". Dictionary of Veterinary Drugs and Animal Health Products Marketed in France, 16th Edition, Les Editions du Point Vétérinaire, 2011, pp. 1658-1661.
Phillips et al., "The challenge of gene therapy and DNA delivery". Journal of Pharmacy and Pharmacology, vol. 53, 2001, pp. 1169-1174.
Piel et al., "Development of a parenteral and of an oral formulation of albendazole with cyclodextrins". S.T.P. Pharma Sciences, vol. 9, No. 3,1999, pp. 257-260.
Pirollo et al., "Targeted Delivery of Small Interfering RNA: Approaching Effective Cancer Therapies". Cancer Research, vol. 68, No. 5, Mar. 2008, pp. 1247-1250.
Rackley, Charles E., "Diseases of the Heart and Pericardium"., The Merck Manual, Chapter 25, 16th Edition, 1992, pp. 446-459.
Redenti et al., "Drug/Cyclodextrin/Hydroxy Acid Multicomponent Systems. Properties and Pharmaceutical Applications" Journal of Pharmaceutical Sciences, vol. 89, 2000, pp. 1-8.
Remme et al., "Hemodynamic Effects of Intravenous Pimobendan in Patients with Left Ventricular Dysfunction". Journal of Cardiovascular Pharmacology, vol. 15, Supp. 2, 1989, pp. S41-S44.
Remme et al., "Hemodynamic, Neurohumoral, and Myocardial Energetic Effects of Pimobendan, a Novel Calcium-Sensitizing

(56) References Cited

OTHER PUBLICATIONS

Compound, in Patients with Mild to Moderate Heart Failure". Journal of Cardiovascular Pharmacology, vol. 24, No. 5, 1994, pp. 730-739.

Rinsyo to Kenkyu, "A case of diastolic hypertrophic cardiomyopathy in which sinus bradycardia and associated cardiac failure were improved as a result of cilostazol administration." The Japanese Journal of Clinical and Experimental Medicine, vol. 83, No. 5, May 2006, pp. 125-130.

Rodriguez, Damon B., "Treatment of Feline Hypertrophic Cardiomyopathy*". Compendium, vol. 24, No. 6, Jun. 2002, pp. 470-476.

Roland et al., "The Use of Pimobendan in Feline Heart Failure Secondary to Spontaneous Heart Disease". The 18th Annual ECVIM Congress, Abstract, Belgium, Sep. 2008, 1 page.

Rudnic et al., "Oral Solid Dosage Forms". Remington: The Science and Practice of Pharmacy, 20th Edition, Lippincott Williams & Wilkins, Baltimore, Maryland, Chapter 45,2000, pp. 858-870.

Saavedra et al., "Reverse Remodeling and Enhanced Adrenergic Reserve From Passive External Support in Experimental Dilated Heart Failure". Journal of the American College of Cariology, vol. 39, No. 12, 2002, pp. 2069-1076.

Sabbah et al., "Effects of long-term monotherapy with enalapril, metoprolol, and digoxin on the progression of left Ventriculardysfuntion and dilation in dogs with reduced ejection fraction". Circulation, vol. 89, 1994, pp. 2852-2859.

Sabbah, Hani N., "The Cardiac Support Device and the Myosplint: Treating Heart Failure by Targeting Left Ventricular Size and Shape". The Annals of Thoracic Surgery, vol. 75, 2003, pp. S13-S19.

Shiga et al., "b-Blocker Therapy Combined with Low-Dose Pimobendan in Patients with Idiopathic Dilated Cardiomyopathy and Chronic Obstructive Pulmonary Disease: Reporton Two Cases". Cardiovascular Drugs and Therapy, vol. 16, 2002, pp. 259-263.

Sisson et al., "Myocardial Diseases of Dogs". Textbook of Canine and Feline Cardiology: Principles and Clinical Practice, Second Edition, Chapter 27, Saunders, 1999, pp. 581-619.

Conlon, P. D., "Nonsteroidal Drugs Used in the Treatment of Inflammation". Veterinary Clinics of North America Small Animal Practice, vol. 18, No. 6, Nov. 1988, pp. 1115-1131.

Cowley et al., "Treatment of severe heart failure: quantity or quality of life? A trial of enoximone", British Heart Journal, vol. 72,1994, pp. 226-230.

Côté et al., "Congestive Heart Failure". Feline Cardiology, Ch. 19, Wiley-Blackwell, ISBN 978-0-8138-1242-7, 2011, 9259.

Deneke et al., "Medikamentose Therapie der Herzinsuffizienz" Herzschr Elektrophys, vol. 15, Suppl 1, 2004, pp. 1/74-1/80.

Dews et al., "The Antihistamine Substance 2786 R.P." British Journal of Pharmacology, vol. 1, 1946, pp. 278-286.

Dictionary of Veterinary Drugs and Animal Health Products Marketed in France, 12th Edition, 2003, 3 pages.

El-Badry et al., "Physicochemical Characterization and Dissolution Properties of Meloxicam-Gelucire 50/13 Binary Systems." Scientia Pharmaceutica, vol. 79, 2011, pp. 375-386.

El-Hagrasy et al., "A Process Analytical Technology Approach to Near-Infrared Process Control of Pharmaceutical Power Blending: Part II: Qualitative Near-Infrared Models for Prediction of Blend Homogeneity". Journal of Pharmaceutical Sciences, vol. 95, No. 2, Feb. 2006, pp. 407-421.

El-Hagrasy et al., "Near-Infrared Spectroscopy and Imaging for the Monitoring of Powder Blend Homogeneity". Journal of Pharmaceutical Sciences, vol. 90, No. 9, Sep. 2001,. pp. 1298-1307.

Elliott, P., "Diagnosis and management of dilated cardiomyopathy". Heart, vol. 83, 2000, pp. 106-112.

Endoh, Masao, "New Aspects of the Treatment of Myocardial Failure from a Pharmacological Standpoint". Journal of Clinical and Experimental Medicine, vol. 187, No. 10, 1998, pp. 827-831.

Erhardt, L., "An Emerging Role for Calcium Sensitisation in the Treatment of Heart Failure". Expert Opinion on Investigational Drugs, vol. 14, No. 6, 2005, pp. 659-670.

Ettinger et al., "Effects of enalapril maleate on survival of dogs with naturally acquired heart failure". Journal of the American Veterinary Medical Association, vol. 213, No. 11, 1998, pp. 1573-1577.

Ettinger et al., "Therapeutic Considerations in Medicine and Disease". Textbook of Veterinary Internal Medicine, Diseases of the Dog and Cat, Sixth Edition, vol. 1,2004, pp. 530-531.

Fasinu et al., "Diverse approaches for the enhancement of oral drug bioavailability." Biopharmaceutics & Drug Disposition, vol. 32, 2011, pp. 185-209.

Fitton et al., "Pimobendan. A Review of its Pharmacology and Therapeutic Potential in Congestive Heart Failure". Drugs and Aging, vol. 4, No. 5, 1994, pp. 417-441.

Fox et al., "Bradykinin-evoked sensitization of airway sensory nerves: A mechanism for ACE-inhibitor cough." Nature Medicine, vol. 2, No. 7, Jul. 1996, pp. 814-817.

Fox et al., "Prosepective Double-Blinded, Multicenter Evaluation of Chronic Therapies for Feline Diastolic Heart Failure: Interim Analysis". ACVIM Abstracts, Abstract 78, 2003, pp. 398-399.

Fox, Philip R., "Hypertrophic Cardiomyopathy. Clinical and Pathologic Correlates". Journal of Veterinary Cardiology, vol. 5, No. 2, Nov. 2003, pp. 39-45.

Fraker et al., "Reversal of phosphate induced decreases in force by the benzimidazole pyridazinone, UD-CG 212 CL, in myofilaments from human ventricle." Molecular and Cellular Biochemistry, vol. 176, 1997, pp. 83-88.

Fuentes, et al., "A Double-Blind, Randomized, Placebo-Controlled Study of Pimobendan in Dogs with Dilated Cardiomyopathy," Journal of Veterinary Internal Medicine, vol. 16, 2002, pp. 255-261.

Fujino et al., "Differential Effects of d- and l-Pimobendan on Cardia Myofilament Calcium Sensitivity1". The Journal of Pharmacology and Experimental Therapeutics, vol. 247, No. 2, 1988, pp. 519-523.

Goineau et al., "Cardiomyopathic Syrian Hamster as a Model of Congestive Heart Failure". Current Protocols in Pharmacology, Supp. 42, Unit 5.50, John Wiley & Sons, Inc., Sep. 2008, 12 pages.

Groban, Leanne, "Diastolic Dysfunction in the Older Heart". Journal of Cardiothoracic and Vascular Anesthesia, vol. 19, No. 2, Apr. 2005, pp. 228-236.

Gwathmey et al., "Abnormal Intracellular Calcium Handling in Myocardium From Patients With End-Stage Heart Failure" Circulation Research, vol. 61, No. 1, 1987, pp. 70-76.

Hasenfuss et al., "Influence of the calcium-sensitizer UDCG-115 on hemodynamics and myocardial energetics in patients with idiopathic dilated cardiomyopathy. Comparison with nitroprusside". Basic Research Cardiology, vol. 84, No. 1, 1989, pp. 225-233.

Hauf et al., "Acute and Long-Term Hemodynamic Effects of Pimobendan (UD-CG 115 BS) in Comparison with Captopril". Journal of Cardiovascular Pharmacology, vol. 15, Supp. 2, 1989, pp. S49-S56.

Hemati et al., "Fluidized bed coating and granulation: influence of process-related variables and physicochemical properties on the growth kinetics". Powder Technology, vol. 13, 2002, pp. 18-34.

Häggstrom et al., "Effect of Pimobendan or Benazepril Hydrochloride on Survival Times in Dogs with Congestive Heart Failure Caused by Naturally Occurring Myxomatous Mitral Valve Disease: The QUEST Study". Journal of Veterinary Internal Medicine, vol. 22, 2008, pp. 1124-1135.

Häggstrom et al., "Longitudinal Analysis of Quality of Life, Clinical, Radiographic, Echocardiographic, and Laboratory Variables in Dogs with Myxomatous Mitral Valve Disease Rexceiving Pimobendan or Benazepril: The QUEST Study". Journal of Veterinary Internal Medicine, 2013, pp. 1-11.

Häggstrom et al., "Effects of long-term treatment with enalapril or hydralazine on the renin-angiotension-aldosterone system and fluid balance in dogs with naturally acquired mitral valve regurgitation". American Journal of Veterinary Research, vol. 57, No. 11, Nov. 1996, pp. 1645-1662.

Häggström et al., "New insights into degenerative mitral valve disease in dogs". Veterinary Clinics Small Animal Practice, vol. 34, 2004, pp. 1209-1226.

International Search Report and Written Opinion for PCT/EP2005/002957 dated Jun. 30, 2005.

Iwasaki et al., "Pimobendan Inhibits the Production of Proinflammatory Cytokines and Gene Expression of Inducible Nitric Oxide

(56) References Cited

OTHER PUBLICATIONS

Synthase in a Murine Model of Viral Myocarditis". Journal of the American College of Cardiology, vol. 33, No. 5, 1999, pp. 1400-1407.
Jain et al., "Effects of Milrinone on Left Ventricular Remodeling After Acute Myocardial Infarction". Circulation, vol. 84, No. 2, Aug. 1991, pp. 798-804.
Kanno et al., "Effects of Pimobendan for Mitral Valve Regurgitation in Dogs." Journal of Veterinary Medical Science, vol. 69, No. 4, Apr. 2007, pp. 373-377.
Kashem et al., "CardioClasp: A New Passive Device to Reshape Cardiac Enlargement". ASAIO Journal, vol. 48, No. 3, 2002, pp. 253-259.
Kato et al., "Clinical Evaluation of Pimobendan (UD-CG115BS) for Chronic Heart Failure-A Multicentre Placebo-Controlled Double Blind Study". Journal of Clinical Therapeutics & Medicines, vol. 8, No. 6, 1992, pp. 1311-1351.
Kato, Kazuzo, "Clinical Efficacy and Safety of Pimobendan in Treatment of Heart Failure-Experience in Japan". Cardiology, vol. 88, Supp. 2, 1997, pp. 28-36.
Katz et al., "A multicenter, randomized, double-blind, placebo-controlled trial of pimobendan, a new cardiotonic and Vasodilator agent, in patients with severe congestive heart failure". American Heart Journal, vol. 123, 1992, pp. 95-103.
Kittleson et al., "The Acute Hemodynamic Effects of Milrinone in Dogs With Severe Idiopathic Myocardial Failure". Journal of Veterinary Medicine, vol. 1, 1987, pp. 121-127.
Kitzen et al., "Pimobendan". Cardiovascular Drug Reviews, vol. 6, No. 4, 1988, pp. 265-291.
Koob et al., "Acute Effects of Furosemide on Blood Electrolytes and Hemodynamics in Dogs". Angiology, 1978, pp. 463-472.
Kubo et al., "Beneficial Effects of Pimobendan on Exercise Tolerance and Quality of Life in Patients with Heart Failure. Results of a Multicenter Trial". Circulation, vol. 85, No. 3, Mar. 1992, pp. 942-949.
Kvart et al., "Efficacy of Enalapril for Prevention of Congestive Heart Failure in Dogs with Myxomatous Valve Disease and Asymptomatic Mitral Regurgitation" Journal of Veterinary Internal Medicine, vol. 16, 2002, pp. 80-88.
Lachman et al., "The Theory and Practice of Industrial Pharmacy"., 3rd Edition, Lea & Febiger, Philadelphia, 1986, pp. 58-60.
Lai et al., "Real Time and Noninvasive Monitoring of Dry Powder Blend Homogeneity". AIChE Journal, vol. 47, No. 11, Nov. 2001, pp. 2618-2622.
Lamb et al., "Assessment of the value of the vertebral heart scale in the radiographic diagnosis of cardia disease in dogs" Veterinary Record, vol. 146, 2000, pp. 687-690.
Lantz et al., "Stability of nizatidine in extemporaneous oral liquid preparations". American Journal of Hospital Pharmacy, vol. 47, No. 12, Dec. 1990, pp. 2716-2719.
Lewis et al., "Near-Infrared Chemical Imaging for Product and Process Understanding", in Process Analytical Technology, Second Edition, John Wiley & Sons, Ltd., United Kingdom, 2010, pp. 272-276.
Sisson, David, "Lecture Notes: Cardiology", The District of Columbia Academy of Veterinary Medicine, May 2001, pp. 1-18.
Stuber et al.,"The Pharmaceutical and Biological Availability of Commercial Preparations of Furosemide". Arzneimittel-Forschung, vol. 32, No. 6, 1982, pp. 693-697.
Summerfield et al., "Efficacy of Pimobendan in the Prevention of Congestive Heart Failure or Sudden Death in Doberman Pinschers with Preclinical Dilated Cardiomyopathy (The PROTECT Study)". Journal of Veterinary Internal Medicine, vol. 26, 2012, pp. 1337-1349.
Sun et al., "Pimobendan." Chemical Industry Press, 2002, pp. 29-30.
Takeda et al., "Normalization of Left Ventricular Parameters Following Combined Pimobendan and Carvedilol Treatment in a Case of Unclassified Cardiomyopathy with Longstanding Refractory Status". Internal Medicine, vol. 41, No. 12, Dec. 2002, pp. 1147-1152.
The American Heritage Dictionary, homogeneous, Last Accessed Feb. 10, 2011, 1 page, http://www.xreferplus.com/entry/hmdictenglang/homogeneous.
Thiel et al., "Content uniformity of microdose tablets (dosage 1 µg 10 mg) produced by fluid bed granulation of nteractive mixtures". Journal of Pharmacy and Pharmacology, vol. 38, 1986, pp. 335-343.
Tomanek et al., "Growth of the Coronary Vasculature in Hypertrophy: Mechanisms and Model Dependence". Cellular and Molecular Biology Research, vol. 40, No. 2, 1994, pp. 129-136.
Trendelenburg, U. "The Action of Histamine and 5-Hydroxytryptamine on Isolated Mammalian Atria". The Journal of Pharmacology and Experimental Therapeutics, vol. 130, No. 4, Dec. 1960, pp. 450-460.
Upadhyay et al., "Formulation of Fast-Release Gastroretentive Solid Dispersion of Glibenclamide with Gelucire 50/13." Tropical Journal of Pharmaceutical Research, vol. 11, No. 3, Jun. 2012, pp. 361-369.
Van Meel et al., "Pimobendan Increases Survival of Cardiomyopathic Hamsters". Journal of Cardiovascular Pharmacology, vol. 13, 1989, pp. 508-509.
Vasconcelos et al., "Solid dispersions as strategy to improve oral bioavailability of poor water soluble drugs." Drug Discovery Today, vol. 12, Nos. 23/24, Dec. 2007, pp. 1068-1075.
Vidal et al., "Making sense of antisense". European Journal of Cancer, vol. 41,2005, pp. 2812-2818.
Villar et al., "Ibuprofen, Aspirin and Acetaminophen Toxicosis and Treatment in Dogs and Cats". Veterinary and Human Toxicology, vol. 40, No. 3, Jun. 1998, pp. 156-162.
Vromans et al., "Densification properties and compactibility of mixtures of pharmaceutical excipients with and without magnesium stearate." International Journal of Pharmaceutics, vol. 46, 1988, pp. 183-192.
Wikipedia, the Free Encyclopedia, "Milrinone". [Accessed at: http://en.wikipedia.org/wiki/Milrinone on Mar. 10, 2014].
Wikipedia, the Free Encyclopedia, "Pimobendan". [Accessed at: http://en.wikipedia.org/wiki/Pimobenan on Mar. 10, 2014].
Woolley et al., "Effects of Treatment Type on Vertebral Heart Size in Dogs With Myxomatous Mitral Valve Disease". The Journal of Applied Research in Veterinary Medicine, vol. 5, No. 1, 2007, pp. 43-48.
Petit et al., "VETMEDIN® 1.25 mg, VETMEDIN® 2.5 mg, VETMEDIN® 5 mg, Inodilatateur (pimobendane) en gelule pour chiens". Dictionnaire Medicaments Veterinaires et des produits de Sante Animale commercialises en France, 16th Edition, Les Editions du Point Veterinaire, 2005, pp. 1257-1257.
Declaration of Professor Adrian Boswood filed Jun. 1, 2018 in the Opposition to European Patent No. 1 951 227 B1.
O'Grady, M. R., et al. "Efficacy of benazepril hydrochloride to delay the progression of occult dilated cardiomyopathy in Doberman Pinschers." Journal of veterinary internal medicine 23.5 (2009): 977-983.
O'Grady, M. R., et al. "Effect of pimobendan on case fatality rate in Doberman Pinschers with congestive heart failure caused by dilated cardiomyopathy." Journal of Veterinary Internal Medicine 22.4 (2008): 897-904.
Consensus Trial Study Group*. "Effects of enalapril on mortality in severe congestive heart failure." New England Journal of Medicine 316.23 (1987): 1429-1435.
"905 Uniformity of Dosage Units". 2011 The United States Pharmacopeial Convention, Stage 6 Harmonization, Dec. 1, 2011, pp. 1-3.
"Cardiovascularsystem". MIMS, IVS Annual, Chapters, 2003, p. 104.
"Citric Acid". The Merck Index, An Encyclopedia of Chemicals, Drugs, and Biologicals, 13th Edition, Merck Research Laboratories Division of Merck & Co., Inc., Whitehouse Station, NJ, Index 2350, 2001, pp. 405-406.
"Guidance for Industry, Container Closure Systems for Packaging Human Drugs and Biologies: Chemistry, Manufacturing, and Controils

(56) References Cited

OTHER PUBLICATIONS

Documentation". U.S. Department of Health and Human Services Food and Drug Administration, May 1999, pp. 1-56.
"Pharmaceutical Necessities". Remington's Pharmaceutical Sciences, 18th Edition, Mack Publishing Company, Easton, Pennsylvania, Chapter 66, 1990, pp. 1288-1300.
"Pimobendan". The Merck Index, An Encyclopedia of Chemicals, Drugs, and Biologicals, 13th Edition, Merck Research Laboratories Division of Merck & Co., Inc., Whitehouse Station, NJ, Index 7515, 2001, p. 1332.
"Rimadyl F 50 mg". Summary of Product Characteristics, Zoetis France, May 15, 2013, pp. 1-4.
"Summary of Product Characteristics: Vetmedin Chew 1.25 mg chewable tablets for dogs." Boehringer Ingelheim Vetmedica GmbH, Feb. 23, 2016, pp. 1-6. [Accessed at: http://bijsluiters.fagg-afmps.be/DownloadLeafletServlet?d=253494].
"Vetmedin® —1,25 mg appetizing tablets for dogs Veterinary use". Summary of Product Characteristics, SCS Boehringer Ingelheim Comm. V, Mar. 25, 2009, pp. 1-4.
Abstract in English for CN1702243A, 2005.
Abstract in English for DE3728244, 1989.
Abstract in English for EP0306846, 1989.
Abstract in English for EP0330052, 1989.
Abstract in English for JP2005281283, 2005.
Abstract in English for JPH0489428, 1992.
Abstract in English of JPH03157314, 1991.
Abstract in English of JPH0570612, 1993.
Abstract in English of JPH11228302, 1999.
Ahmed et al., "Pharmaceutical challenges in veterinary product development". Advanced Drug Delivery Reviews, vol. 54, 2002, pp. 871-882.
Asanoi et al., "Disparate Inotropic and Lusitropic Responses to Pimobendan in Conscious Dogs with Tachycardia-Induced Heart Failure" Journal of Cardiovascular Pharmacology, vol. 23, No. 2, 1994, pp. 268-274.
Ash et al., "Receptor Mediating Some Actions of Histamine". British Journal of Pharmacology and Chemotherapy, vol. 27, No. 2, Aug. 1996, pp. 427-439.
Atkins et al., "Guidelines for the Diagnosis and Treatment of Canine Chronic Valvular Heart Disease". Journal of Veterinary Internal Medicine, vol. 23, No. 6, 2009, pp. 1-9.
Atkins et al., "Pharmacologic management of myxomatous mitral valve disease in dogs." Journal of Veterinary Cardiology, vol. 14, 2012, pp. 165-184.
Banker et al., "Uniformity of Dosage Units". Modern Pharmaceutics, Fourth Edition, Revised and Expanded, Marcel Dekker, Inc., New York, NY, 2006, p. 498.
Bassani et al., "Enhanced Water-Solubility of Albendazole by Hydroxy-Propyl-ß-Cyclodextrin Complexation". Journal of Inclusion Phenomena and Molecular Recognition in Chemistry, vol. 25, No. 1-3, Mar. 1996, pp. 149-152.
Bastien et al., "Chronic AT receptor blockade and angiotensin-converting enzyme (ACE) inhibition in (CHF 146) cardiomyopathic hamsters: effects on cardiac hypertrophy and survival". Cardiovascular Research, vol. 43, 1999, pp. 77-85.
Baur et al., "Cardiac remodelling and myocardial contractility in patients with congestive heart failure treated with furosemide and enalapril" Basic Research in Cardiology, vol. 86, Supp. 1, 1991, pp. 157-163.
Beaufrere et al., "Therapeutic Review: Pimobendan." Journal of Exotic Pet Medicine, vol. 18, No. 4, Oct. 2009, pp. 311-313.
Beers, et al., Merck Manual of Diagnosis and Therapy, 17th Edition, Chapter 203, Section 16, Merck Research Laboratories, Whitehouse Station, NJ, USA, 1999, pp. 1688-1692.

Berny et al., "Review: Animal Poisoning in Europe. Part 2: Companion Animals". The Veterinary Journal, vol. 193, 2010, pp. 255-259.
Black et al., "Definition and Antagonism of Histamine H2-receptors". Nature, vol. 236, Apr. 1972, pp. 385-390.
Boehringer Ingelheim Vetmedica GmbH, 1st International Canine Valvular Disease Symposium, Paris, Oct. 30-31, 2004, pp. 1-45.
Boehringer Ingelheim Vetmedica, Inc. "Freedom of Information Summary: Original New Animal Drug Application". NADA 141-273, Vetmedin, Pimobendan Chewable Tablets, Apr. 30, 2007, pp. 1-46.
Borgarelli et al., "Canine Idiopathic Dilated Cardiomyopathy. Part II: Pathophysiology and therapy". The Veterinary Journal, vol. 162, 2001, pp. 182-195.
Boswood et al., "Effect of Pimobendan in Dogs with Preclinical Myxomatous Mitral Valve Disease and cardiomegaly: the EPIC Study-A Randomized Clinical Trial." Journal of Veterinary Internal Medicine, vol. 30,2016, pp. 1765-1779.
Boswood et al., "Evaluation of pimobendan in dogs with cardiomegaly caused by preclinical mitral valve disease." The Veterinary Record, vol. 168, No. 8, Feb. 2011, p. 222.
Bourezg et al., "Redispersible lipid nanoparticles of Spironolactone obtained by three drying methods." Colloids and Surfaces A: Physicochemical and Engineering Aspects, vol. 413,2012, pp. 191-199.
Bozzone, Scott, "Solid Oral Dosage Forms Powder Blending" and "Solid Oral Dosage Forms, Blend Uniformity Principles and Examples". Pfizer, IKEV Meeting, May 31, 2001, pp. 1-66.
Brewster et al., "Cyclodextrins as pharmaceutical solubilizers". Advanced Drug Delivery Reviews, vol. 59, No. 7, 2007, pp. 645-666.
Buchanan et al. "Vertebral scale system to measure canine heart size in radiographs". Journal of the American Veterinary Medical Association, vol. 206, No. 2, Jan. 1995, pp. 194-199.
Burlage et al., "Other Pharmaceutical Adjuncts"., Physical and Technical Pharmacy, The Blakiston Division: The McGraw-Hill Book Company, Inc., New York, 1963, pp. 653-662.
Calvert et al., "Congestive cardiomyopathy in Doberman Pinscher dogs". Journal of the American Veterinary Medical Association, vol. 181,1982, pp. 598-602.
Calvert et al., "Signalment, Survival, and Prognostic Factors in Doberman Pinschers With End-Stage Cardiomyopathy". Journal of Veterinary Internal Medicine, vol. 11, No. 6, 1997, pp. 323-326.
Cambridge Dictionary, homogeneous, Last Accessed Feb. 10, 2011, 1 page, http://dictionary.cambridge.org/dictionary/british/homogeneous.
Chambers 21st Century Dictionary, homogeneous, Last Accessed Feb. 10, 2011, 1 page, http://www.xreferplus.com/entry/chambdict/homogeneous.
Chetboul, et al., "Comparitive Adverse Cardiac Effects of Pimobendan and Benazepril Monotherapy in Dogs with Mild Degenerative Mitral Valve Disease: A Prospective, Controlled, Blinded, and Randomized Study". Journal of Veterinary Internal Medicine, vol. 21, 2007, pp. 742-753.
Chiang, Chung-Seung, "Management of Congestive Heart Disease." Medical Session, vol. 7, No. 8, Oct. 2002, pp. 4-9.
Choy et al., "Scaling of myocardial mass to flow and morphometry of coronary arteries". Journal of Applied Physiology, vol. 104, 2008, pp. 1281-1286.
Cohn et al., "Cardiac Remodeling-Concepts and Clinical Implications: A Consensus Paper From an International Forum on Cardiac Remodeling" Journal of the American College of Cardiology, vol. 35, No. 3, 2000, pp. 569-582.
Collins English Dictionary, homogeneous, Last Accessed Feb. 10, 2011, 1 page, http://xreferplus.com/entry/hcengdict/homogeneous.

* cited by examiner

PDE III INHIBITORS FOR TREATMENT OF ASYMPTOMATIC HEART FAILURE

CROSS-REFERENCE TO RELATED APPLICATIONS

This application is a continuation under 35 U.S.C. § 120 of U.S. patent application Ser. No. 13/832,292, filed Mar. 15, 2013 (now issued as U.S. Pat. No. 10,117,869), which is a continuation under 35 U.S.C. § 120 of U.S. patent application Ser. No. 12/482,481, filed Jun. 11, 2009 (now issued as U.S. Pat. No. 8,980,894), which is a continuation-in-part under 35 U.S.C. § 120 of U.S. patent application Ser. No. 11/559,467, filed Nov. 14, 2006 (now abandoned), which is a continuation-in-part under 35 U.S.C. § 120 of U.S. patent application Ser. No. 11/087,465, filed Mar. 23, 2005 (now U.S. Pat. No. 9,463,199), which claims priority under 35 U.S.C. § 119 to European Patent Application No. 04007179, filed Mar. 25, 2004, and to European Patent Application No. 05110689, filed Nov. 14, 2005. The disclosures of these patent applications are incorporated herein by reference in their entireties.

FIELD OF THE INVENTION

The invention relates to the use of a phosphodiesterase type III (PDE III) inhibitor or a "$Ca^{2+}$-sensitizing agent" or a pharmaceutically acceptable derivative thereof for the preparation of a medication for the reduction of the heart size of a patient suffering from heart failure, and a medication for the reverse remodeling of the heart of a patient with asymptomatic (occult) heart failure and their delayed onset of clinical symptoms.

BACKGROUND OF THE INVENTION

Heart failure is divided in different stages (ISACHC-Stages-Class I-III). The pathology of the heart begins with ISACHC Class I in which cardiac murmur or cardiac chamber enlargement, but no clinical symptoms are present (Class I or occult stage). Heart insufficiency scoring is used herein, and the following is a description of the scoring so used.

Degree of heart insufficiency was evaluated using a 5-class score adapted from the International Small Animal Cardiac Health Council (ISACHC) System of Heart Failure Classification:

Class I: The Asymptomatic Patient (Heart Disease Associated with No Clinical Signs)
  Heart disease is detectable (e.g. cardiac murmur, arrhythmia, or cardiac chamber enlargement that is detected by radiography or echocardiography); however the patient is not overtly affected and does not demonstrate clinical signs of heart failure. The need for treatment at this stage is arguable but not justifiable with currently available data.
  The stage is subdivided as follows:
  A.: Signs of heart disease are present but no signs of compensation (volume or pressure overload ventricular hypertrophy) are evident (Class IA).
  B.: Signs of heart disease are present and signs of compensation (volume or pressure overload ventricular hypertrophy) are detected radiographically or echocardiographically (Class IB).
Class II: Mild-to-Moderate Heart Failure
  Clinical signs of heart failure are evident at rest or with mild exercise, and adversely affect the quality of life. Typical signs of heart failure include exercise intolerance, cough, tachypnoea, mild respiratory distress (dyspnoea), and mild to moderate ascites. Hypoperfusion at rest is generally not present (Class II). Home treatment is often indicated at this stage.
Class III: Advanced Heart Failure
  A.: Clinical signs of advanced congestive heart failure are immediately obvious. These clinical signs could include respiratory distress (dyspnoea), marked ascites, profound exercise intolerance, or hypoperfusion at rest. In the most severe cases, the patient is moribund and suffers from cardiogenic shock. Death or severe debilitation is likely without therapy.
  B.: Patients with advanced heart failure are divided into two Subcategories:
    1. Home care is possible (Class IIIA).
    2. Hospitalization is mandatory (cardiogenic shock, life-threatening oedema, or a large pleural effusion is present) (Class IIIB).

It is known that the progress of heart failure is associated with an increase of the size of the heart. In dilated cardiomyopathy (DCM), the ratio of left ventricular wall thickness to chamber diameter is decreased and the circumferences of the annuluses of the mitral and tricuspid valves are increased in proportion to the magnitude of chamber dilation. DCM may either be caused primarily, e.g. by genetic abnormalities, or secondarily, e.g. due to valvular insufficiency, both resulting in cardiac volume overload. However, it involves usually cardiac remodeling that may be defined as genome expression, molecular, cellular, and interstitial changes manifested clinically as changes in size, shape, and function of the heart. Cardiac remodelling is generally an adverse sign and linked to heart failure progression. Reverse cardiac remodelling is a goal of the treatment of heart failure therapy.

Heart failure therapy has traditionally focused largely on symptomatic relief rather than on addressing underlying disease problems. Many dogs with symptomatic DCM have a very guarded prognosis (Monnet et al., 1995), with Dobermanns in particular generally experiencing only short survival times (Calvert et al., 1982; Calvert et al., 1997). There have been few studies examining the influence of treatment on survival in dogs with symptomatic DCM, although a subanalysis of the dogs with DCM in the LIVE study showed an improvement in time to treatment failure in those dogs receiving enalapril compared with placebo (142.8 versus 56.5 days, respectively) (Ettinger et al., 1998). On the whole, oral positive inotropic agents have lost favour in the treatment of chronic heart failure in human patients in recent years, after a number of trials revealed adverse effects on survival despite short-term hemodynamic benefits (Packer et al., 1991; Cowley and Skene, 1994). Recently it has been suggested that calcium sensitizing agents may result in positive inotropic effects without producing some of the adverse effects (including calcium overload) associated with more traditional positive inotropes such as dobutamine, amrinone and milrinone.

In ISACHC Class I stage heart failure, in which cardiac murmur or cardiac chamber enlargement, but no clinical symptoms are present, therapy would have two objectives: reduce the pathologic changes of the dimensions of the heart (to the normal parameters—"reverse remodeling"); and prolong the time until onset of clinical symptoms.

However, there is currently no drug available which has proven to be efficacious in the reduction of the pathologic changes of the dimensions of the heart to the normal parameters ("reverse remodeling") at asymptomatic stage (ISACHC Class I). A study has been published with the use of ACE-Inhibitors in the asymptomatic stage, but no therapeutic effect was shown (SVEP Trial), neither a reverse remodeling nor a prolongation of the time until onset of clinical symptoms.

When the pathology progresses and clinical symptoms are also present (Class II or III), several drugs showed a benefit in quality of life and some also in survival time. These drugs include phosphodiesterase type III (PDE III) inhibitors or "$Ca^{2+}$-sensitizing agents", for example cilostazol, pimobendan, milrinone, levosimendan, amrinone, enoximone and piroximone TZC-5665, etc. Rather than increasing calcium entry into cardiac myocytes, calcium sensitisers achieve their positive inotropic effect by sensitizing the contractile proteins to existing cytosolic calcium, by altering the binding of calcium with troponin-C. Producing a positive inotropic effect by calcium sensitizing thereby avoids some of the adverse effects of cytosolic calcium overload. Increased cytosolic calcium levels have been associated with an increased tendency for arrhythmias and sudden death. Clinical trials of long-term use of oral pimobendan in human patients with heart failure have demonstrated an improvement in exercise tolerance and quality of life without significantly adverse effects on survival (Kubo et al., 1992; Katz et al., 1992).

The problem underlying the present invention was to provide a medication, which increases the time without clinical symptoms and remodels the size of the heart to reduce the risk of death in patients with asymptomatic heart disease (ISACHC Class I).

SUMMARY OF THE INVENTION

It has surprisingly been found that phosphodiesterase type III (PDE III) inhibitors and/or $Ca^{2+}$-sensitizing agents, preferably pimobendan, or pharmaceutically acceptable derivatives thereof can be used for the preparation of a medication able to prolong the time until onset of clinical symptoms and for the reduction of the heart size in cases of asymptomatic (occult) heart failure, e.g. asymptomatic DCM.

Moreover, the invention relates to a method of reduction of the heart size in cases of asymptomatic (occult) heart failure, e.g. asymptomatic DCM, which method comprises administering to a patient having an asymptomatic heart failure, e.g. asymptomatic DCM, an effective amount of a PDE III inhibitor, preferably pimobendan, or a pharmaceutically acceptable derivative thereof.

Furthermore, the invention relates to an article of manufacture comprising packaging material contained within which is a composition effective to prolong the time until onset of symptoms and to reduce the heart size of a patient having an asymptomatic (occult) heart failure, e.g. asymptomatic DCM, and the packaging material comprises a label which indicates that the composition can be used to prolong the time until onset of symptoms and to reduce the heart size of a patient having an asymptomatic (occult) heart failure, e.g. asymptomatic DCM, wherein said composition comprises at least one PDE III inhibitor or a $Ca^{2+}$-sensitizing agent, preferably pimobendan, or a pharmaceutically acceptable derivative thereof.

DETAILED DESCRIPTION OF THE INVENTION

Figure 1:
FIG. 1 shows the lateral thoracic radiograph of an English cocker spaniel with dilated cardiomyopathy, showing alveolar pulmonary oedema and cardiac enlargement.
Figure 2A:
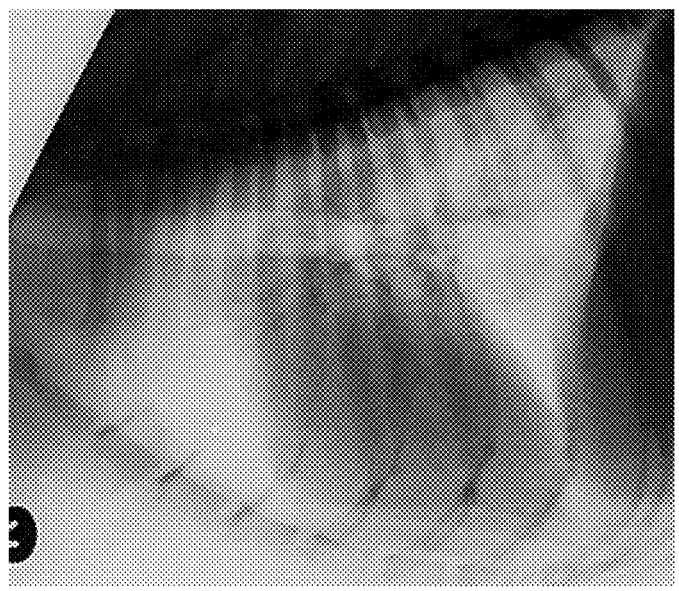
FIGS. 2a and 2b show the thoracic radiograph of the same dog in FIG. 1, following four months treatment with furosemide, enalapril, digoxin, and pimobendan.
Figure 2B:
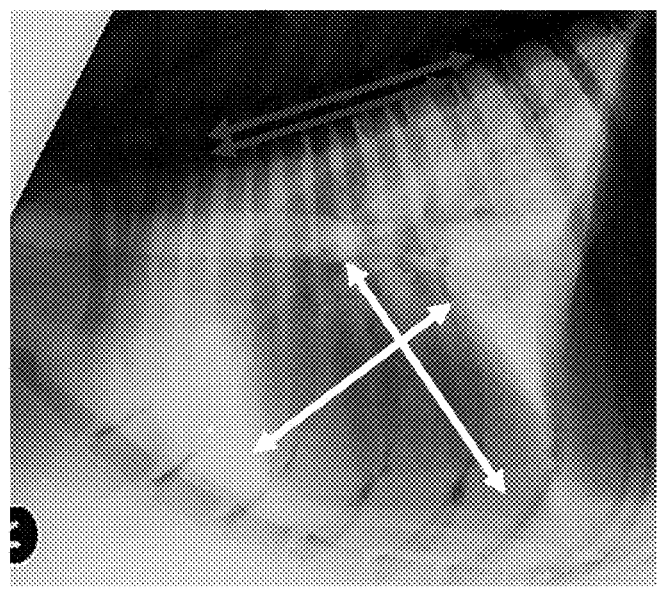
Figure 3:
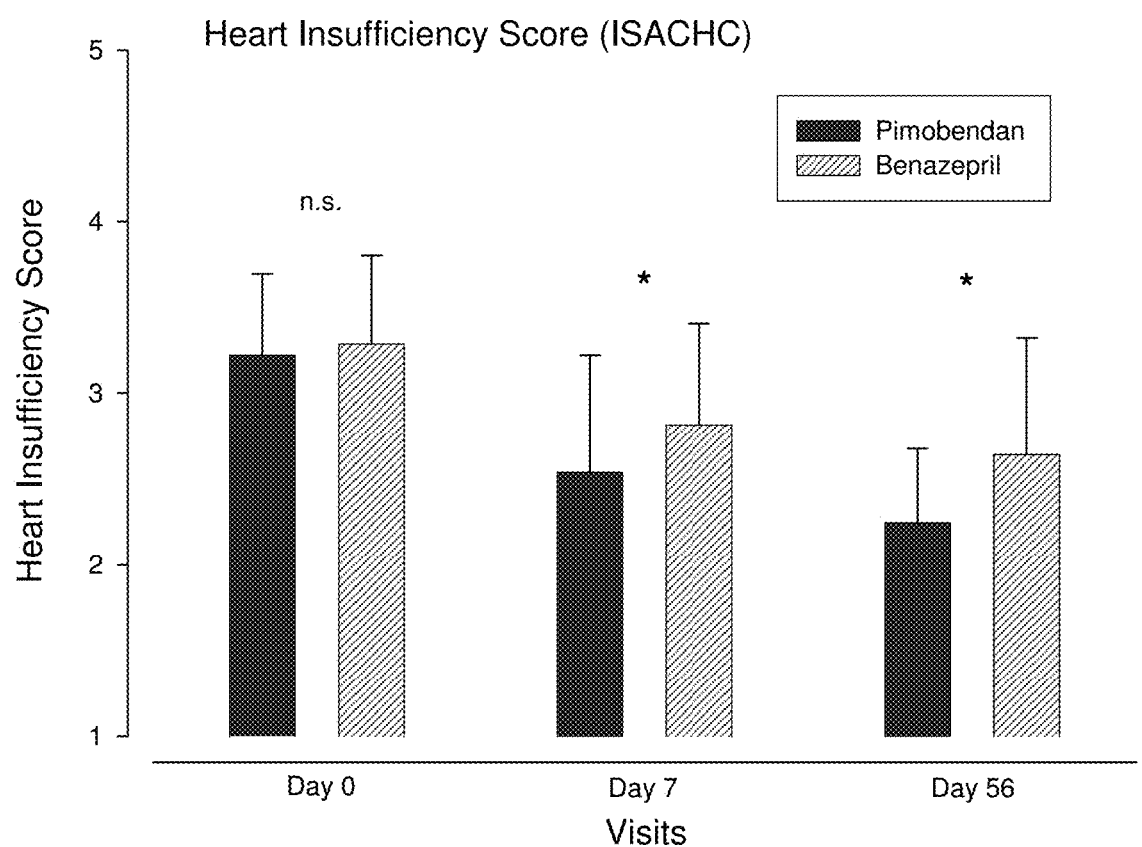
FIG. 3 shows the Heart Insufficiency Score (ISACHC) in dogs treated with pimobendan (each left black column) or benazepril (each right grey column) on days 0, 7 and 56.
Figure 4:
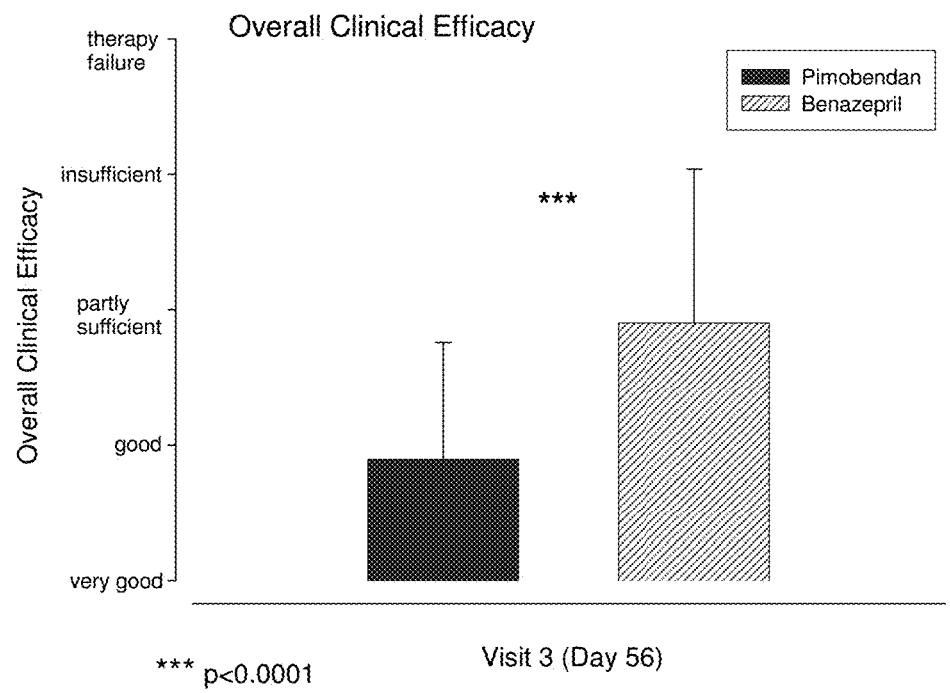
FIG. 4 shows the Overall Clinical Effect in dogs treated with pimobendan (left black column) or benazepril (right grey column) on day 56.
Figure 5:
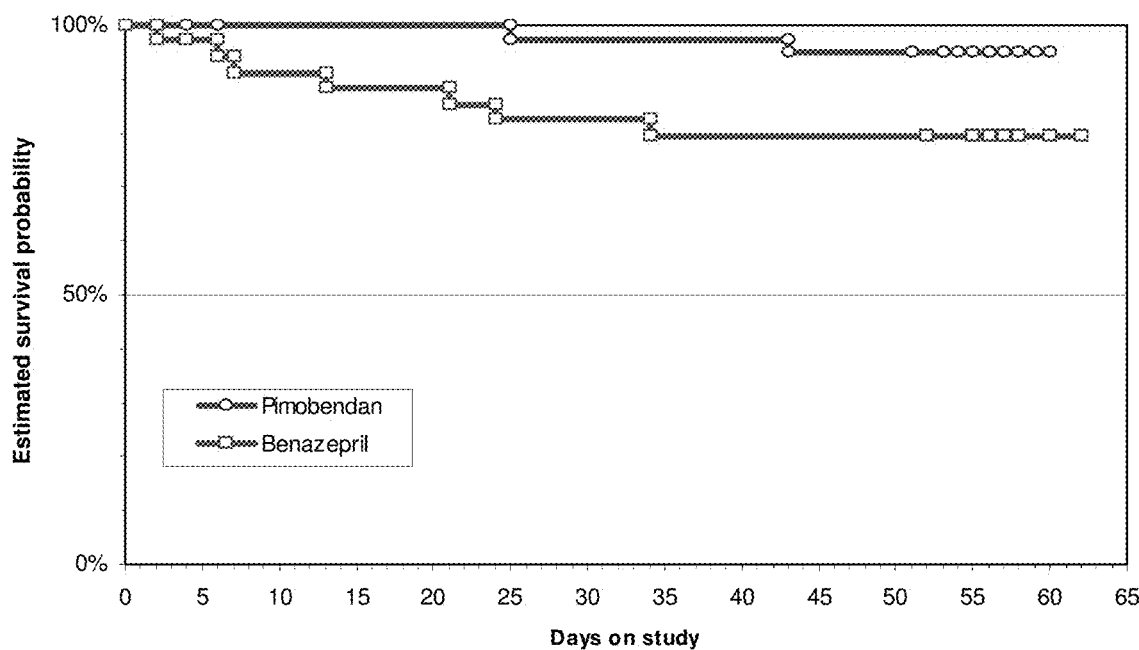
FIG. 5 shows the survival function (56-day period) in dogs treated with pimobendan (upper -○- curve) or benazepril (lower -□- curve).
Figure 6:
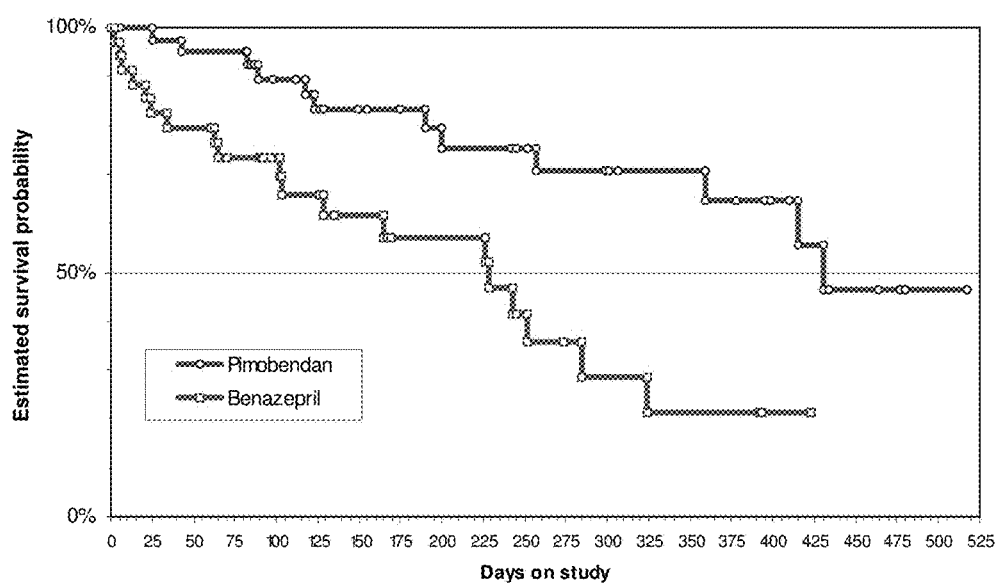
FIG. 6 shows the survival function in dogs treated with pimobendan (430-day period/upper -○- curve) or benazepril (228-day period/lower -□- curve).

The invention relates to the use of a phosphodiesterase type III (PDE III) inhibitor, preferably a PDE III inhibitor, a $Ca^{2+}$-sensitizing agent, or a PDE III inhibitor which exhibits additionally calcium sensitizing effects ($Ca^{2+}$-sensitizing agent), or a pharmaceutically acceptable derivative thereof for the preparation of a medication for the prolongation of the time until onset of clinical symptoms of the heart disease and the reduction of the heart size of a patient having an asymptomatic (occult) heart failure, e.g. asymptomatic DCM.

The term "PDE III inhibitor" as used hereinabove and hereinbelow relates to phosphodiesterase (PDE) III inhibitors, which prevent breakdown of cAMP to 5'AMP and thus maintain the effect of cAMP on protein kinase and other secondary messenger activation.

The effects of PDE III inhibitors are as a rule positive inotropy and vasodilatation, which reduces the afterload and makes patients with heart failure feel better.

The term $Ca^{2+}$-sensitizing agent relates to a compound which increases the Ca.sup.2+ sensitivity of cardiac contractile proteins, i.e., increase the developed contractile force at a given concentration of $Ca^{2+}$.

Preferred PDE III inhibitors or $Ca^{2+}$-sensitizing agents are cilostazol, pimobendan, milrinone, levosimendan, amrinone, enoximone and piroximone TZC-5665 or pharmaceutically acceptable salts, derivatives, metabolites or pro-drugs thereof. Most preferred are pimobendan and levosimendan, or pharmaceutically acceptable salts, derivatives, metabolites or pro-drugs thereof. Even more preferred is pimobendan and levosimendan. Even more preferred is pimobendan, pharmaceutically acceptable salts, derivatives, metabolites or pro-drugs thereof.

Pimobendan, known to the public as 4,5-dihydro-6-[2-(4-methoxyphenyl)-1H-benzimidazol-5-yl]-5-methyl-3(2H)-pyridazone, is for example disclosed in EP 008 391 B1. Levosimendan is a pyridazone-dinitrile derivative known to the public as (R)-[[4-(1,4,5,6-Tetrahydro-4-methyl-6-oxo-3-pyridazinyl)phenyl]hydrazono-]propanedinitrile, which has been described earlier for example in GB 2228004, U.S. Pat. Nos. 5,151,420 and 5,569,657.

The term "patient" as used hereinabove and hereinbelow relates to an animal or a person having symptomatic, e.g., DVM, or asymptomatic (occult) heart failure, e.g. asymptomatic DCM. The term "patient" embraces mammals such as primates including humans.

In addition to primates, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species.

Preferred are human patients, dogs, cats and horses. Human patients are female or male persons, having symptomatic or asymptomatic (occult) heart failure, e.g. asymptomatic DCM. As a rule such persons are children, young adults, adults or elderly people with an age of between 6 and 80, preferably between 30 and 65 years.

The term "heart failure" as used hereinabove and hereinbelow relates to any contractile disorder or disease of the heart. Clinical manifestations are as a rule the results of changes to the heart's cellular and molecular components and to mediators that drive homeostatic control. Heart failure is as a rule accompanied by an increase of the heart size and deterioration of cardiac functions. Predominantly, the patients suffer from heart failure that is a chronic congestive heart failure, a heart failure due to myocardial infarction or myocardial ischemia due to cardiac arrest.

The term "asymptomatic heart disease" as used hereinabove and hereinbelow relates to any contractile disorder or disease of the heart without clinical symptoms of heart failure. In particular, it relates to heart failure of ISACHC-Stages-Class I. More particular, it relates to a DCM of ISACHC-Stages-Class I.

The term "reduction of the heart size" as used hereinabove and hereinbelow relates to a reduction of the size of the heart of a patient, which is diagnosed using echocardiography, or according to the radiograph methods suggested by James W. Buchanan et al. (Buchanan 1995). The reduction is expressed in the relative change of the vertebral heart size. Preferably for a symptomatic patient, the relative mean vertebral heart sum (VHS) of said patient is reduced by 0.05 to 0.25 within 10 to 100 days, in particular by about 0.15 within about 60 days, of treatment with the PDE III inhibitor and/or $Ca^{2+}$-sensitizing agent.

The term "prolongation until onset of clinical symptoms" as used hereinabove and hereinbelow relates to the time from diagnosing the changes of the heart until the beginning of clinical symptoms of heart failure. In particular, it relates to the prolongation from heart failure of ISACHC Class I to Class II and further to Class III. It more particular relates to the prolongation from heart failure of DCM of ISACHC Class I to Class II and further to Class III.

The term "effective amount" as used herein means an amount sufficient to achieve a prolongation of the time until onset of clinical symptoms and reduction of the heart size when said PDE III inhibitor or $Ca^{2+}$-sensitizing agent is administered in a single dosage form.

According to a further embodiment of the present invention, the PDE III inhibitor and/or $Ca^{2+}$-sensitizing agent is administered in combination with a second active therapeutic agent. Such a second active therapeutic agent is preferably selected from the group consisting of calcium channel blockers, ACE inhibitors, diuretics, platelet inhibitors, beta blockers and angiotensin II antagonists, aldosterone antagonists, *digitalis* glycosides, anti-arrhythmic agents or diuretics, and in particular:

wherein the calcium channel blocker inhibitor is selected from the group consisting of diltiazem, verapamil and felodipine or a pharmaceutically acceptable derivative thereof; and/or wherein the ACE inhibitor is selected from the group consisting of omapatrilat, MDL100240, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, trandolapril, trandolaprilat, ceranapril, moexipril, quinaprilat and spirapril or a pharmaceutically acceptable derivative thereof; and/or wherein the beta blocker is selected from the group consisting of bisoprolol, carvediol, metoprolol, propranolol and timolol or a pharmaceutically acceptable derivative thereof; and/or wherein the angiotensin II antagonist is selected from the group consisting of saralasin acetate, candesartan, cilexetil, valsartan, candesartan, losartan potassium, eprosartan, irbesartan, tasosartan, pomisartan and telmisartan or a pharmaceutically acceptable derivative thereof; and/or wherein the aldosterone antagonist is selected from the group consisting of spironolactone, eplerenone, canrenone, potassium canrenone or a pharmaceutically acceptable derivative thereof, and/or wherein the anti-arrhythmic agents are selected from the group consisting of amiodarone, betrylium, disopyramide, dofetilide, flecamide, ibutilide, mexiletine, tocainide, procainamide, propafenone, quinidine, sotalol or a pharmaceutically acceptable derivative thereof, and/or wherein the diuretic is selected from the group consisting of furosemide, torasemide, bumetanide, etacrynic acid, azosemide, muzolimine, piretanide, tripamide, bendroflumethazide, chlorothiazide, hydrochlorothiazide, hydroflumethazide, methychlothiazide, polythiazide, trichlormethiazide, chlorthialidone, indapamide, metolazone, quinethazone, etozolin, triamteren, amiloride, or a pharmaceutically acceptable derivative thereof; and/or wherein the *digitalis* glycosides is selected from the group consisting of digoxin, digitoxin, g-strophantin, β-methyldigoxin, β-acetyldigoxin or a pharmaceutically acceptable derivative thereof.

Most preferably, the PDE III inhibitor or $Ca^{2+}$-sensitizing agent, preferably pimobendan or levosimendan, even more preferred pimobendan is administered together with one or more medicaments selected from the group consisting of one or more ACE-inhibitors, one or more diuretics and one or more *digitalis* glycosides.

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, preferably of pimobendan or levosimendan, when used for the indicated effects, will range between about 10 μg/kg to 10 mg/kg, preferably from 0.05 mg/kg to 5 mg/kg, in particular from 0.1 mg/kg to 2 mg/kg. Most preferably from about 0.1 mg/kg to 1.5 mg/kg of pimobendan are administered per day.

The PDE III inhibitors and/or $Ca^{2+}$-sensitizing agents may be administered in a single daily dose, or the total daily dosage may be administered in divided doses of two, three, or four times daily.

The PDE III inhibitors and/or $Ca^{2+}$-sensitizing agents can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The PDE III inhibitors and/or $Ca^{2+}$-sensitizing agents are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and colouring agents can also be incorporated into the mixture. Suitable binders include starch, gelatine, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The PDE III inhibitors and/or $Ca^{2+}$-sensitizing agents can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The PDE III inhibitors and/or $Ca^{2+}$-sensitizing agents may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues.

Furthermore, the PDE III inhibitors and/or $Ca^{2+}$-sensitizing agents may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and cross linked or amphipathic block copolymers of hydrogels.

Dosage forms (pharmaceutical compositions) suitable for administration may contain from about 1 milligram to about 100 milligrams of active ingredient per dosage unit.

In these pharmaceutical compositions the active ingredient will ordinarily be present in an amount of about 0.5-95% by weight based on the total weight of the composition.

Gelatine capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Where two or more of the foregoing second therapeutic agents are administered with the PDE III inhibitor and/or $Ca^{2+}$-sensitizing agent, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when two therapeutic agents are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients.

Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Procedures by way of example for preparing the compositions according to the invention will be described in more detail hereinafter. The Examples which follow serve solely as a detailed illustration without restricting the subject matter of the invention. The study was done in symptomatic dogs.

Example 1

A double-blind study has been carried out in order to evaluate the long-term efficacy and tolerance to pimobendan and its effect on long-term survival in cocker spaniels and Dobermanns with DCM.

Materials and Methods: Cocker spaniels (n=10) and Dobermanns (n=10) presenting to the Cardiopulmonary Service of the R(D)SVS with DCM were recruited for the study with owners' consent. After stabilization on conventional therapy with digoxin, enalapril, and furosemide, dogs received in addition either pimobendan (Vetmedin®) or placebo using a double-blind study design.

Results: The mean survival time for cocker spaniels on pimobendan was 612 days (range 61-1428) compared to 589 (range 51-1127) for the placebo group. The difference was not statistically significant (Wilcoxon-Mann-Whitney-U test, $p>0.05$).

The mean survival time for Dobermanns on pimobendan was 280 days (range 42-369) compared to 72 days (range 13-196) for the placebo group. The difference was statistically significantly different (Student's t-test, $p<0.05$). The drug was well tolerated and no treatment-related adverse effects were noted in either breed.

Conclusion: Pimobendan significantly improved the survival time of the Dobermanns with DCM compared with placebo, but had no statistically significant effect on survival of the cocker spaniels. The improved survival time for the Dobermanns is an important development in the management of a disease that generally results in rapid death following diagnosis.

In both breeds the addition of pimobendan to a standard treatment regimen was associated with a significant improvement of the NYHA-class status of the patient. The benefit of pimobendan therapy was therefore additive to the beneficial effect of furosemide, enalapril and digoxin, and was even seen in the cocker spaniels which had what would be considered a favorable clinical course with conventional therapy, compared with many dogs with DCM (Monnet et al., 1995).

A striking difference in survival times was found in the Doberman pinschers treated with pimobendan. Although this breed is known to have a poor prognosis after development of congestive signs, a significant prolongation of survival time was found for pimobendan-treated animals.

Example 2

A double-blind randomized positive controlled multi-centre field trial has been carried out in order to evaluate the clinical efficacy of pimobendan treatment at a daily dose of 0.4-0.6 mg/kg in comparison to an angiotensin-converting-enzyme (ACE) inhibitor treatment with benazepril hydrochloride at a daily dose of approximately 0.25-0.5 mg/kg body weight. Both treatments could be combined with furosemide (up to 8 mg/kg per day) or anti-arrhythmic drugs as appropriate. The study was conducted at 11 centers in Europe by experienced veterinary cardiologists under the rules of Good Clinical Practice (GCP). Mandatory minimum duration of treatment was 56 days for each patient. Dogs were examined on Day 0 prior to first treatment and on Day 7 and 56 after initiation of therapy. In order to obtain long-term survival data, the investigator had the option to continue therapy after Day 56. In the optional study period treatment code for the animal was decoded, as it was not allowed to add pimobendan to the benazepril group, in order to maintain an appropriate pimobendan control group. All other licensed concomitant therapies were allowed. For survival analysis, animals that dropped out or changed treatment due to therapy failure were also rated as dead. However, these cases were statistically evaluated as censored data.

Primary parameter for conclusion on efficacy was the clinical severity of heart failure symptoms, classified according to the recommendations of the International Small Animal Cardiac Health Council (ISACHC). Secondary parameters were exercise tolerance, demeanor, findings of the respiratory and circulatory system, overall efficacy rating, as well as, echocardiography data.

Overall 76 dogs, 41 dogs in the pimobendan group and 35 dogs in the benazepril group were included. All dogs showed clinically overt symptoms of heart failure due to valve insufficiency. Mean duration of symptoms prior to inclusion was 4.05 months in the pimobendan and 2.77 months in the benazepril group. There were no clinically relevant differences between the groups prior to initiation of therapy in any of the parameters investigated.

The primary parameter, ISACHC heart failure classification, was improved in 84% of the pimobendan treated cases but only in 56% of the benazepril cases after the 56 day treatment period. At this time point ISACHC classification Ib (Score=2), i.e., no clinical symptoms, was reported for 76% of the pimobendan but only 48% of the benazepril cases. Differences between the groups regarding the primary parameter, were statistically significant in favor of pimobendan on Day 7 ($p=0.0280$) and Day 56 ($p=0.0201$). Consequently, overall efficacy was rated as very good or good in 85% of the pimobendan cases but only in 41% of the benazepril cases ($p<0.0001$). Results in other secondary parameters were in accordance with the clinical results of the heart failure classification.

In the 56-days study period, 2 dogs in the pimobendan group and 7 in the benazepril group died or were euthanised due to cardiac reasons. Survival analysis according to Kaplan-Meier revealed significant differences in favor of pimobendan ($p=0.0386$). Analysis of long-term survival data confirmed the results of the 56-day period. Median survival time for pimobendan treated dogs was 430 days versus 228 days for dogs that received no pimobendan. Again, survival analysis according to Kaplan-Meier revealed significant differences in favor of pimobendan ($p=0.0020$).

The radiographs have been made in a left to right lateral view. For the determination of cardiac size a vertebral scale system was used.

In the lateral radiographs, the long axis of the heart (L) was measured with a caliper extending from the ventral aspect of the left main stem bronchus (tracheal bifurcation hilus, carina) to the most distant contour of the left ventricular apex. The caliper was repositioned along the vertebral column beginning at the cranial edge of the 4.sup.th thoracic vertebra. The length of the heart was recorded as the number of vertebrae caudal of that point and estimated to the nearest 0.1 of a vertebra. The maximum perpendicular short axis (S) was measured in the same manner beginning at the 4.sup.th thoracic vertebra.

The length in vertebrae (v) of the long and short axes were then added to obtain a vertebral heart sum (VHS) which provided a single number representing heart size proportionate to the size of the dog. The normal range of VHS in healthy dogs is 8.5 v to 10.5 v (mean of 9.7 v).

Figure 7:
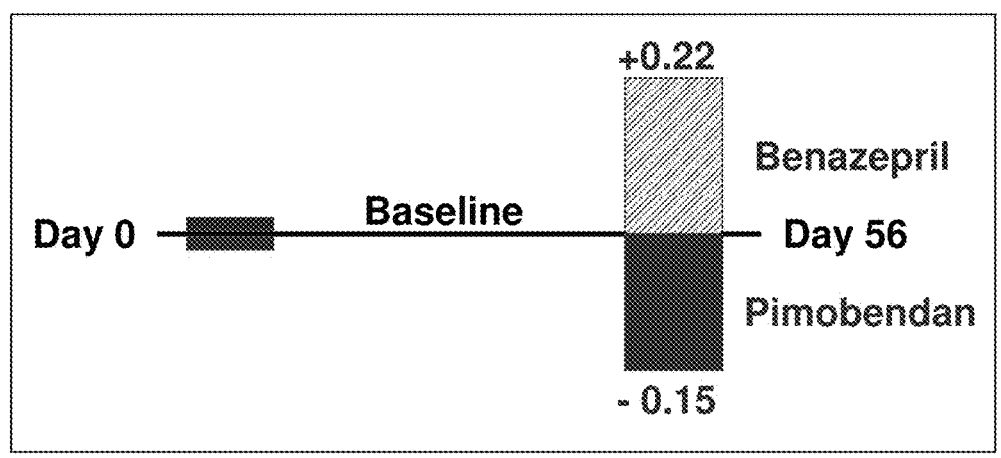
FIG. 7 shows reduction in mean heart size for pimobendan treated dogs (−0.15 v) versus benazepril treated dogs (+0.22 v).

The mean vertebral heart sum measured on radiographs on days 0 and 56 showed improvement for dogs in the pimobendan group. With regards to the changes from baseline, the difference in the mean value indicated a reduction in mean heart size for pimobendan treated dogs. The mean difference between the groups regarding overall clinical efficacy was statistically significant in favor of pimobendan treatment (p<0.0001). See Table 1. The mean scores in the control benazepril group showed deterioration with regard to changes from baseline (FIG. 7). This demonstrates that a reduction of heart size cannot routinely be achieved with standard therapy in dogs with heart failure due to valve insufficiency. The striking difference between standard therapy (ACE-inhibitor+/− diuretics) deterioration of mean heart size by 0.22 v and pimobendan treatment with an improvement of mean size of −0.15 v was unexpected and thus inventive.

TABLE 1

Vertebral scale system - heart sum.

| Visit | Group | N | Min. | Max. | Median | Mean | SD |
|---|---|---|---|---|---|---|---|
| 1 | 1 | 41 | 9 | 14.5 | 11.60 | 11.83 | 1.31 |
| 3 | 1 | 37 | 9.0 | 14.1 | 11.60 | 11.71 | 1.18 |
| 3-1 | 1 | 37 | −1.9 | 0.8 | 0.00 | −0.15 | 0.57 |

Example 3

A study is done with pimobendan (Vetmedin®) in dogs suffering of occult dilated cardiomyopathy.

Inclusion criteria were dogs which are diagnosed to have a congestive heart failure of class I according to the ISACHC-score due to dilated cardiomyopathy (DCM). Dogs having a having an asymptomatic (occult) heart failure, e.g. asymptomatic DCM must have reduced contractility of the heart or other signs of reduced cardiac efficacy such as volume overload or ventricle dilatation as confirmed by echocardiography. The dogs stay under mono-therapy until signs of congestive heart failure are developing, deteriorate to heart insufficiency score (ISACHC) class II or III a or b. After confirmation of the congestion by X-ray—radiography the dogs receive furosemid treatment or if the clinical or echocardiographic results makes the addition of another heart failure treatment necessary (primary endpoint). The dogs will be investigated at day 0 prior to first treatment and then approximately 3 month post initiation of the therapy. In order to get long time survival data the investigators' makes then control visits will be repeated every 3-6 months. An Echo is performed prior to initiation of therapy (Day 0) and at the following visits to support the clinical diagnosis and to evaluate the effect of the drugs on the contractility of the heart. The echocardiography is performed according to the cardiologic case report form for Irish Wolfhounds. The primary parameter investigated will be the heart insufficiency score (ISACHC). Other parameters will be exercise tolerance, findings of the respiratory and circulatory system as well as echocardiography data.

Results:

After 4 years the interim analysis showed that significantly less dogs treated with pimobendan went into the state of clinical symptoms (Class II)

A Left Ventricular Reverse Remodeling (LVRR,=Normalizing of the size and function of the left ventricle) has been shown in dogs treated with Pimobendan (ca 80%).

Since other studies in dogs with asymptomatic heart failure with other drugs could not show a prolongation until onset of clinical symptoms these results were unexpected and thus inventive. Furthermore no other study has been shown in dogs with asymptomatic heart disease a reverse remodeling in heart failure and thus the results were unexpected and thus inventive.

REFERENCES

Buchanan J W, et al. Vertebral Scale System to measure canine heart size in radiographs, JAVMA, Vol. 206, No. 2, 194-199

Calvert, C. A., Chapman, W. C., and Toal, R. C. (1982) Congestive cardiomyopathy in Doberman Pinscher dogs, Journal of the American Veterinary Medical Association 181: 598-602.

Calvert, C. A., Pickus, C. W., Jacobs, G. J., and Brown, J. (1997) Signalment, survival, and prognostic factors in Doberman Pinschers with end-stage cardiomyopathy, Journal of Veterinary Internal Medicine 11: 323-326.

Cohn J N, et al. (2000) Cardiac Remodeling—Concepts and Clinical implications: A Consensus Paper From an International Forum on Cardiac Remodeling, J. of the American College of Cardiology, Vol. 35, No. 3, 569-582

Cowley, A. J. and Skene, A. M. (1994), Treatment of severe heart failure: quantity or quality of life? A trial of enoximone, British Heart Journal 72: 226-230.

Ettinger, S. J., Benitz, A. M., Ericsson, G. F., Cifelli, S., Jernigan, A. D., Longhofer, S L, Trimboli, W., and Hanson, P. D. (1998), Effects of enalapril maleate on survival of dogs with naturally acquired heart failure. The Long-Term Investigation of Veterinary Enalapril (LIVE) Study Group, Journal of the American Veterinary Medical Association 213: 1573-1577.

Katz, S. D., Kubo, S. H., Jessup, M., Brozena, S., Troha, J. M., Wahl, J., Cohn, J. N., Sonnenblick, E. H., and LeJemtel, T. H. (1992), A multicenter, randomized, double-blind, placebo-controlled trial of pimobendan, a new cardiotonic and vasodilator agent, in patients with severe congestive heart failure, American Heart Journal 123: 95-103.

Kubo, S. H., Gollub, S., Bourge, R., Rahko, P., Cobb, F., Jessup, M., Brozena, S., Brodsky, M., Kirlin, P., and Shanes, J. (1992), Beneficial effects of pimobendan on exercise tolerance and quality of life in patients with heart failure. Results of a multicenter trial. The Pimobendan Multicenter Research Group. Circulation 85: 942-949.

Monnet, E., Orton, E. C., Salman, M., and Boon, J. (1995), Idiopathic dilated cardiomyopathy in dogs: survival and prognostic indicators. Journal of Veterinary Internal Medicine 9: 12-17.

Packer, M., Carver, J. R., Rodeheffer, R. J., et al, and for the PROMISE Study Research Group (1991), Effect of oral milrinone on mortality in severe chronic heart failure. New England Journal of Medicine 325: 1468-1475.

What is claimed:

1. A method for treating a patient suffering from ISACHC (International Small Animal Cardiac Health Council) Classification Class I heart failure, the method comprising:
    administering to the patient a therapeutically effective amount of pimobendan or a pharmaceutically acceptable salt thereof;
    wherein the administration results in a reduction in the size of the patient's heart.

2. The method of claim 1, wherein the ISACHC Classification Class I heart failure is asymptomatic (occult) dilated cardiomyopathy (DCM).

3. The method of claim 1, wherein pimobendan is administered to the patient in oral or parenteral form.

4. The method of claim 1, wherein pimobendan is administered to the patient in a daily dose from 10 µg/kg to 10 mg/kg.

5. The method of claim 1, wherein the administering step has the further effect of causing a prolongation of the time until the onset of clinical symptoms of ISACHC Classification Class II or ISACHC Classification Class III heart failure in the patient.

6. The method of claim 1, wherein the patient is a mammal selected from the group consisting of primates, dogs, cats and horses.

7. The method of claim 1, wherein the patient is a mammal selected from the group consisting of dogs, cats and horses.

8. The method of claim 1, wherein the patient is a dog.

9. A method for prolongation of the time until onset of clinical symptoms in a patient having ISACHC (International Small Animal Cardiac Health Council) Classification Class Ib heart failure, the method comprising administering to the patient a therapeutically effective amount of pimobendan or a pharmaceutically acceptable salt thereof.

10. The method of claim 9, wherein the patient has asymptomatic (occult) dilated cardiomyopathy (DCM).

11. The method of claim 9, wherein pimobendan is administered to the patient in oral or parenteral form.

12. The method of claim 9, wherein pimobendan is administered to the patient in a daily dose from 10 µg/kg to 10 mg/kg.

13. The method of claim 9, wherein said administering step has the further effect of causing a reduction in the size of the heart of the patient.

14. The method of claim 9, wherein the patient is a mammal selected from the group consisting of primates, dogs, cats and horses.

15. The method of claim 9, wherein the patient is a mammal selected from the group consisting of dogs, cats and horses.

16. The method of claim 9, wherein the patient is a dog.

17. A method for treating a patient suffering from ISACHC (International Small Animal Cardiac Health Council) Classification Class I heart failure, the method comprising:
    administering to the patient a therapeutically effective amount of a phosphodiesterase type III (PDE III) inhibitor comprising pimobendan or a pharmaceutically acceptable salt thereof;
    wherein the administration results in a reduction in the size of the patient's heart.

18. A method for treating a dog suffering from asymptomatic heart disease, the method comprising administering to the dog a therapeutically effective amount of pimobendan or a pharmaceutically acceptable salt thereof, wherein the therapeutically effective amount is effective to delay a time until onset of congestive heart failure in the dog.

* * * * *